(12) United States Patent
Hallett

(10) Patent No.: US 8,316,847 B2
(45) Date of Patent: Nov. 27, 2012

(54) AUTOMATIC POSITIVE AIRWAY PRESSURE THERAPY THROUGH THE NOSE OR MOUTH FOR TREATMENT OF SLEEP APNEA AND OTHER RESPIRATORY DISORDERS

(75) Inventor: Michael David Hallett, Pyrmont (AU)

(73) Assignee: Ventific Holdings Pty Ltd, Pyrmont, SW (AU)

( * ) Notice: Subject to any disclaimer, the term of this patent is extended or adjusted under 35 U.S.C. 154(b) by 1236 days.

(21) Appl. No.: 11/845,797

(22) Filed: Aug. 28, 2007

(65) Prior Publication Data
US 2009/0095297 A1    Apr. 16, 2009

(30) Foreign Application Priority Data

Sep. 1, 2006    (AU) ................................ 2006904770

(51) Int. Cl.
*A61M 16/00*    (2006.01)
*A62B 7/00*    (2006.01)

(52) U.S. Cl. ......... 128/204.18; 128/204.21; 128/204.22; 128/204.23; 128/204.26; 128/206.21

(58) Field of Classification Search ............. 128/204.18, 128/204.21, 204.22, 204.23, 204.26, 205.25, 128/200.24
See application file for complete search history.

(56) References Cited

U.S. PATENT DOCUMENTS

| | | | | |
|---|---|---|---|---|
| 5,117,819 A * | 6/1992 | Servidio et al. | ......... | 128/204.18 |
| 5,148,802 A * | 9/1992 | Sanders et al. | ........... | 128/204.18 |
| 5,503,146 A * | 4/1996 | Froehlich et al. | ........ | 128/204.23 |
| 5,803,066 A * | 9/1998 | Rapoport et al. | ........ | 128/204.23 |
| 6,484,719 B1 * | 11/2002 | Berthon-Jones | ......... | 128/204.23 |
| 6,588,422 B1 * | 7/2003 | Berthon-Jones et al. | | 128/204.23 |
| 2002/0148466 A1 * | 10/2002 | Berthon-Jones | ......... | 128/200.24 |

FOREIGN PATENT DOCUMENTS

WO    WO 2005065757 A1 *    7/2005

* cited by examiner

*Primary Examiner* — Clinton T Ostrup
(74) *Attorney, Agent, or Firm* — Young Law Firm, P.C.

(57) ABSTRACT

A method of providing ventilatory support or treatment of sleep disordered breathing, implemented using an electrically operated and computer controlled fan or blower, a gas delivery tube, and an atmospherically vented face mask or nasal prongs. The method, over a single respiratory cycle, includes cycling administered pressure between and including an upper pressure and a lower pressure to a user's airway. The lower pressure is greater than atmospheric pressure and is maintained only for as long as is required to allow the immediately prior administered gas volume to be at least substantially expelled from the user's respiratory system by its elastic recoil. The lower pressure is immediately thereafter returned to the upper pressure.

11 Claims, 4 Drawing Sheets

AUTOMATIC POSITIVE AIRWAY PRESSURE THERAPY THROUGH THE NOSE OR MOUTH FOR TREATMENT OF SLEEP APNEA AND OTHER RESPIRATORY DISORDERS

CROSS REFERENCE TO RELATED APPLICATIONS

This application claims foreign priority benefits under 35 U.S.C. §119(a)-(d), of Australian Patent Application No. 2006904770, filed 2006-09-01.

BACKGROUND TO THE INVENTION

Positive pressure therapies include nasal continuous positive airway pressure (CPAP) as used in the treatment of obstructive sleep apnea (OSA) and nasal intermittent positive pressure ventilation for breathing support in chronic restrictive and obstructive lung diseases and associated acute exacerbations. A user will wear a nasal or nose mouth mask connected by a tube or flexible conduit connected to a positive pressure air flow generator. The mask system consists of a flexible mask cushion, which also acts as a gasket to prevent loss of gas pressure inside the mask, attached to a mask frame or manifold and attached to the user's head via a head strap or head gear. The mask assembly usually covers the nose but can also cover both the nose and mouth to circumvent mouth leaks and breathing. Alternatively, the mask device may be designed to sit superficially on or be partially inserted into the user's nares.

The general purpose of the apparatus consisting tubing, mask and pressure generator or source is to maintain a positive gas pressure, typically between 0 and 40 centimeters of water (cm H2O), but most practically between 4 and 20 cm H2O, within the user's airway to improve or facilitate gas exchange within the gas exchanging areas of the lung and/or prevent collapse of the upper or non-exchanging parts of the upper airway. Most commonly a single pressure (CPAP) will be used to treat sleep apnea, while 2 pressures can be used to expand and deflate the lungs where ventilatory support is required in cases of respiratory insufficiency. This technique may also have a role to improve comfort in treatment of sleep apnea.

Treatment of OSA, using positive pressure techniques, is often prescribed using fixed CPAP, with the pressure preset in a sleep laboratory. Alternatively, an automatic machine may be used with an ability to provide CPAP where pressure is continuously, gradually and automatically adjusted during a treatment session in response to upper respiratory air flow characteristics, such as the shape of the inspiratory flow time curve; presence of snore or associated pressure and flow changes or overt apnea. Once established, treatment is routinely used in the home.

Alternatively a separate pressure may be applied during inspiration and a lower pressure used for expiration such as described in U.S. Pat. No. 5,148,802. In this case the pressures will be preset and the transition from one pressure to another will be initiated by the patient as they move through inspiration to expiration and vice versa. The rational for this modality is that the patient will find the exhalation pressure lower and hence more comfortable to breathe against, particularly in sleep apnea. In addition the device augments ventilation in addition to providing positive pressure by assisting with movement of air into and out of the lungs by successive pressure inflation and deflation. This will be useful where the patient has some lung insufficiency or muscular deficiency either in combination with or absence of upper airway instability.

Currently automatic selection of pressures for this bi-level modality is limited or difficult particularly during sleep where ventilatory support for hypoventilation syndromes (or hyperventilation/hypoventilation syndromes such as Cheyne Stokes Respiration) and sleep apnea must be managed simultaneously (complex sleep apnea); in sleep apnea the expiratory pressure needed to negate airway closure at the immediate transition from the expiratory pause to inspiration must be set in conjunction with ventilatory support parameters. In automatically controlled CPAP, that is having expiratory and inspiratory pressures set equally, it is possible to set this pressure by simply monitoring inspiratory flow behaviour as discussed above. Typically the 2 pressures will be established manually in a controlled study wherein the user is monitored and the pressures adjusted to achieve the desired treatment outcomes which can include control of sleep apnea as well maintaining ventilatory requirements A further method of support for providing respiratory assistance in respiratory impairment is described in U.S. Pat. No. 4,773,411. In this technique, termed airway pressure release ventilation (APRV), support is provided substantially by CPAP to enhance residual functional capacity with periodic release of pressure to provide passive reduction of lung volume. This periodic release is not breath to breath and the user will typically breathe spontaneously at the preset CPAP pressure. Settings are manually selected by attendants, that is the CPAP level, the release level and release duration as well the number of breaths depending on the patient's respiratory state and hence is suited to attended or in hospital situations and is not designed for treating simple or complex sleep apnea.

During quiet breathing without pressure assistance, such as during sleep or awake involuntary, or spontaneous, breathing, there is a pronounced period of respiratory quiescence whereby the elastic recoil of the lungs and chest wall returns the lungs to their functional residual capacity (FRC). In response to chemoreceptor activity the diaphragmatic muscles, principally, will be innervated to increase negative intrapleural pressure thereby expanding the lung volume. Normally this activity is under autonomic control but during the awake state it may be overridden and air may be moved consciously into and out of the lungs by diaphragmatic and intercostal muscles. In this sense respiration is distinguished from other life sustaining functions, such as heart rate, cardiac contractility and pressure which are entirely within the control of the autonomic system and the individual only has indirect control over these parameters.

Respiratory rate and duration is under control of the respiratory centre located in the reticular substance of the medulla oblongata and pons. These centres respond to changes in blood gas levels and acidity either directly or indirectly through peripheral chemoreceptors. Functionally it may be divided into three neuronal groups comprising the dorsally located inspiratory area, ventrally located expiratory area and the pneumotaxic area of the pons. Normally the rhythmic nature of breathing is controlled principally by the inspiratory area. Neurones in this area are able to oscillate spontaneously in a crescendo like manner gradually increasing intensity causing the diaphragm to contract and causing an inspiratory movement. This gradual increase lasts about 2 seconds in quiet breathing. Conversely during expiration, the inspiratory area becomes dormant for about 3 seconds and the cycle repeats. During normal quiet breathing the expiratory area remains substantially dormant as exhalation is possible through elastic recoil of the lung and chest wall, although some muscular innervation may be present to control smoothness of expiration to prevent expiratory heave, such as seen during sighs and other involuntary movements to for example rebalance atelectic regions in the lungs.

During nasal CPAP therapy, for treatment of sleep apnea for example, we have 2 important observations. First the lungs are expanded by an amount proportional to the compliance of the lungs and chest wall and the applied air pressure. Hence, the FRC is increased over that observed when the user is breathing at atmospheric pressure. This can be described by the following $$FRC(CPAP) = FRC\ atm + \Delta V_{CPAP} \quad (1)$$

Where FRC (CPAP)=functional residual capacity on CPAP

FRC atm=functional residual capacity at atmospheric pressure $\Delta V_{CPCP}$=change in lung volume after CPAP is applied Normal compliance for lungs and chest wall is about 0.13 liters/cm H20. Hence at 10 cm H2O this delta volume is in the vicinity of 1.3 liters. This figure may be reduced for restrictive diseases, however most sleep apnea patients and those with obstructive pulmonary diseases will have normal or near normal lung and thoracic compliance. To place this in perspective, tidal volume during quiet breathing is about 500 ml. Hence we can see that CPAP at therapeutic levels distends the lungs by more the twice the tidal volume, and will reduce the inspiratory reserve volume.

Second, CPAP for many users, as seen for example in those receiving treatment for sleep apnea, feels unnatural and in some uncomfortable. This is often described as discomfort of having to breathe out against the CPAP pressure. For this reason, an alternative to CPAP is to provide a lower pressure during expiration, so called bi-level treatment as discussed. The problem with this modality is that it is not simple to automatically determine the optimal minimum or expiratory pressure level needed to prevent airway closure at the transition from expiration to inspiration if user initiated.

Based on these observations it is possible to postulate that during quiet breathing on CPAP, the breathing cycle is reversed or partly reversed. That is inspiratory cycle occurs to a varying degree by positive pressure inflation/recoil and expiration by innervation of expiratory muscles as opposed to elastic recoil.

In this case equation 1 may be more appropriately written as equation 2

$$IRV(CPAP) = TLC - (FRC\ atm + \Delta V_{CPAP}) \quad (2)$$

Where

TLC=total lung capacity

IRV=inspiratory reserve volume

CPAP=applied pressure which limits inspiratory drive for quiet breathing.

Since expiration, in the absence of CPAP, is by passive recoil in quiet breathing, this may explain some of the discomfort during routine CPAP, for example, that is expiration now requires active muscular effort. Another factor may be the continuous expansion of the lungs and chest wall by CPAP. This observation, however, is complicated by virtue of the fact that respiration can be overridden by voluntary effort. The unnatural sensation of CPAP during consciousness may lead to an "abnormal" voluntary or cortical response. However, if we assume that involuntary exhalation during CPAP use occurs against pressure recoil, this would then suggest that the medullary inspiratory area can be down regulated to interplay with the expiratory centre to maintain background respiratory rate (however respiratory control is further complicated by the pneumotaxic centre located in the pons which acts to either inhibit or uninhibit the inspiratory centre). A further explanation is related to stretch receptors within the walls of the bronchi and bronchioles which if over stretched, as may be seen during CPAP therapy, further limit inspiratory effort particularly during involuntary quiet breathing and sleep. This is known as the Hering-Breuer reflex and is known to become important once the lung volume is increased by about 1.5 liters above FRC; this would appear to be consistent with therapeutic CPAP levels.

However, CPAP treatment remains broadly crude and variably tolerated. While acceptable for most severely affected patients, more comfortable and physiologic solutions are seen as essential to ensure an otherwise effective therapy does not itself become self-limiting for a very debilitating and widespread condition. Furthermore, complex sleep apnea requires more complex solutions to provide background ventilatory support as well as sleep apnea treatment. Finally automatic selection of pressures simplifies prescription and remains adapative to a specific user's needs.

SUMMARY OF THE INVENTION

According to the present invention there is provided a method of providing ventilatory support or treatment of sleep disordered breathing through an atmospherically vented mask or nasal prongs, said method comprising the steps of:

cycling administered pressure between and including an upper pressure and a lower pressure to a user's airway through the vented mask or nasal prongs, said lower pressure being greater than atmospheric pressure and maintained only for sufficient time to allow a prior administered gas volume to be at least substantially expelled from a user's respiratory system by its elastic recoil, the lower pressure immediately thereafter being returned to the upper pressure;

sensing either flow or pressure to detect the user's need to initiate lung emptying and thereby initiating a transition from the upper pressure to the lower pressure, or initiating said transition in response to a minimum background expiratory rate;

applying the upper and lower pressures to the user's airway through the vented mask or nasal prongs.

DETAILED DESCRIPTION OF THE PREFERRED EMBODIMENT

Figure 1A:
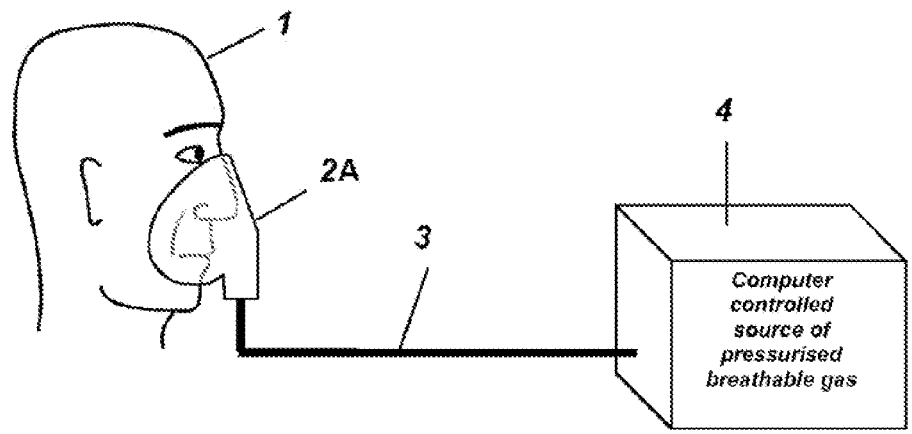
FIG. 1A: Typical apparatus employing the method described by the preferred embodiment of the invention.
Figure 1B:
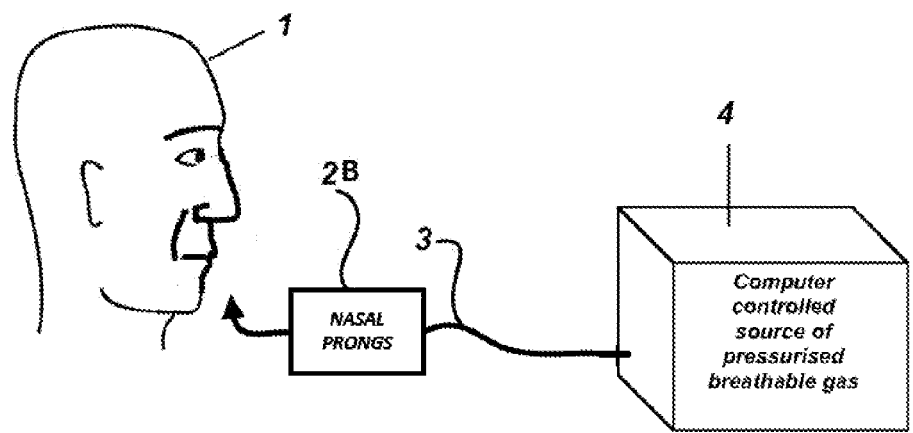
FIG. 1B: Typical apparatus employing the method described by the preferred embodiment of the invention.

A device comprising an automatically adjusting pressure source of breathable gas, a delivery tube and a face mask in communication with a user's airway through nose or mouth is described and shown in FIG. 1A. A device comprising an automatically adjusting pressure source of breathable gas, a delivery tube and nasal prongs in communication with a user's airway through nose is described and shown in FIG. 1B. The user 1 wears a nose or nose mouth mask 2A (FIG. 1A) or nasal prongs 2B (FIG. 1B) connected to air delivery tube 3 in turn connected to pressure source 4. The pressure source would normally be an electronically or electrically operated computer controlled fan or blower supplying a range of delivered pressures from atmospheric pressure up to 40 cm water pressures. Typical pressures would range between 0 and 20 cm H20 with the lowest employable pressure being dependent on carbon dioxide removal characteristics of the mask used. Pressures may be varied by either controlling the fan speed or by employing a spill valve to dump air to atmosphere either in isolation or in conjunction with varying the fan speed. These pressures would be ideally set and administered automatically by the algorithm contained within the computer program of the device. The device is designed to simultaneously treat sleep apnea, periodic breathing or hypoventilation in any combination of severity in spontaneously breathing patients either awake or asleep.

While the invention in the preferred embodiment described herein makes use of a vented face mask, tubing, and a blower unit, in common with other related nasal positive pressure therapies, the blower unit of the invention is designed to provide a more comfortable means for treating sleep apnea or other respiratory disorder such as sleep hypoventilation or COPD, by means of automatic respiratory support. The device is intended primarily, but not limited to use in the unanaesthetised patient in quiet breathing in either wakefulness or sleep. The invention in the preferred embodiment may be effectively used with a CPAP mask, full face mask, mouth mask, or nasal prongs or any combination thereof or any known mask systems for CPAP or nasal ventilation.

Figure 2:
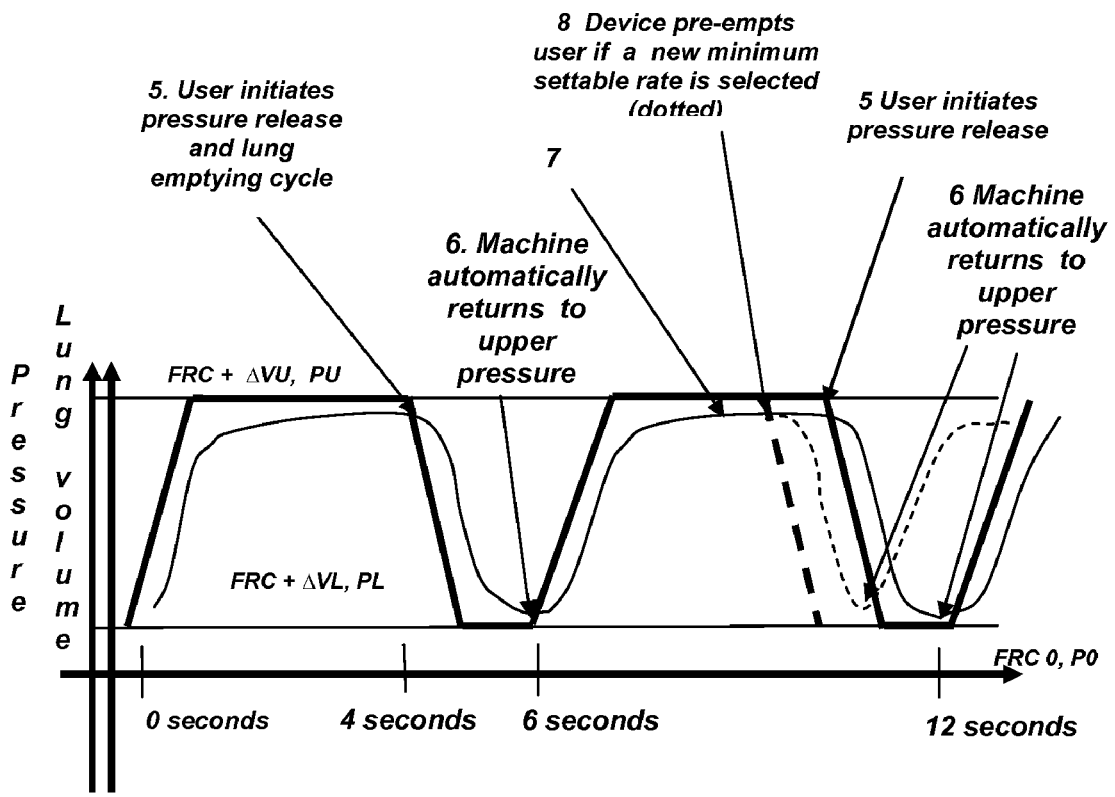
FIG. 2: Possible lung volume and applied pressure versus time profile based on volume change for delivered pressures between Plower (PL) and Pupper (PU) cm H2O.

The invention in the preferred embodiment in part takes advantage of the expiratory pause of the respiratory cycle and provides a means of reversing the normal expiratory/inspiratory cycle such that expiratory pause is transferred to the end of the inspiratory cycle. In this way the patient is not required to "trigger" the inspiratory phase. A typical breathing pattern is shown in FIG. 2 where FRC 0 is residual reserve capacity at atmospheric (0 pressure) during quiet breathing. Transition to higher pressure after lung deflation is performed by the device and based on expired volume and/or flow time profile. Expiratory volume versus time profile is dependent on the elastic recoil properties of the lungs and chest wall, the delivered pressure time profile, the level of obstruction or flow restriction within the lungs (and upper airway if flow limited) and expiratory/inspiratory muscle activity if present. In uncomplicated sleep apnea it may assumed that lungs will be unobstructed and exhibit normal out flow at low pressures although upper airway flow may be obstructed. In practice it is expected the pressure time profile will be provided to provide optimal expiratory emptying prior to reinflation, having regard for patient synchronisation, comfort and ventilatory adequacy. FIG. 2 shows volume versus time for quiet servo controlled breathing and profile may vary. Heavy line represents administered pressure, lighter line represents lung volume. Times are illustrative only and may be shorter or longer than shown.

In FIG. 2 at 5 pressure release occurs on each patient triggered (cycled) or initiated expiration. At 6 the device automatically reinflates the lung after a desired expired volume has been achieved (calculated to prevent lung hyperinflation). This has a further advantage of eliminating need for user triggering to an upper pressure which is inherently insensitive due to hysteresis and need to avoid false triggering. At 7 inspiratory efforts at an upper pressure level are minimised by providing sufficient background minute ventilation through pressure release and activating stretch receptors at an appropriate level of lung inflation above normal FRC to down regulate inspiratory effort. In absence of monitoring airway instability as a means to provide closed loop feedback control of an administered pressure, minimisation of inspiratory effort is important in sleep apnea to provide airway stability. In the context of the invention minimisation of inherent effort is also important during hyperventilation in periodic breathing. At 8 the machine is able to pre-empt an expiratory impulse by timed backup.

The observations discussed in the previous section lead to the possibility of controlling inherent respiration indirectly by activating and deactivating, for example the stretch receptors to control or down regulate inspiratory effort or by provision of machine ventilation. The invention in the preferred embodiment then consists of a servo controlled flow generator attached to a mask attached to the users nose and or mouth. The device will be able to monitor respiratory in and out flow, as well as mask pressure, and vent and mask leak. The device would be able to provide a level of inspiratory support sufficient for normal quiet breathing but could be designed to operate under a broad range of operational conditions depending on the motor and power supply of the blower unit Typically 12 breaths per minute with tidal volume for each breath of 500 milliliters would be provided. The minimum default release pressure level would be set in the range 0 and 4 cm H2O, but its operational range would be settable automatically by the device depending on air out flow characteristics or air trapping within the patient's airway and ventilatory requirements and need to eliminate carbon dioxide. This could be achieved for example by monitoring volume or outflow and when reaching a suitable minimum, close to zero in the case of outflow, the pressure minimum would be set at this level. This would principally be undertaken to reduce unnecessary work of the pressure source and provide a close match with a user's airway requirements. This may also be important in ensuring smooth flow transitions when the upper airway becomes spontaneously closed. However, determining this pressure, while potentially desirable is not considered essential for the satisfactory operation of the device.

The device may be used with mask and venting means described in the prior art. It should also be evident to those skilled in the art that the method described would be optimally administered using a mask venting system that actively and substantially directs expired air to atmosphere. This preferred mask venting system is different to a conventional system that more simply relies upon expired air to accumulate in the air delivery tube and interface before being expelled to atmosphere through a series of passive vents before the next inspiration or lung inflation.

Pressure swing, that is the difference between the upper pressure and the lower pressure will govern the degree of provided ventilation or pressure support. It is clear that this swing must be superimposed on the minimum pressure. Hence the maximum and minimum pressures are further defined by the required swing or ventilatory support. Ventilation would be governed by the rate, tidal volume and average minute ventilation and based on average quiet, stable breathing levels, say over the past 2 to 10 minutes. This eliminates the influence of temporary increases in users effort due to sighs and yawns for example and provide more stable ventilatory control. The device is designed to pace or work at a user's own respiratory rate based on expiratory effort or impetus. Once cycled by expiratory effort the pressure will fall at a predetermined profile possibly under servo control, and once a given volume or flow target has been exhaled and/or pressure reached the unit will automatically cycle back to the preexpiratory pressure level.

The preexpiratory level (the upper pressure level) will be set based on information about the required minute ventilation, and presence of residual inspiratory effort, which may include, for example, presence of snoring or presence of repeated residual inflows in absence of machine support (constant pressure). The presence of single sighs and yawns would be excluded from setting the upper pressure as these are necessarily aimed at improved gas exchange with the lungs e.g atelectasis. As discussed previously during CPAP treatment the Hering-Breuer effect will help to limit further patient inspiratory effort and lung inflation, however further inspiratory effort may indicate need for more ventilatory support or increased rate. This will partially be indicated by expiratory rate set by the user's own respiratory system within the medulla oblongata. In this way information from the user's respiratory centre is indirectly derived from the user's intrinsic rate and need for residual inspiratory effort.

The device aims to find the optimal pressure swings and rate for ventilation to support flow of air into and out of the lungs based on full ventilatory support (no or limited inspiratory effort on part of the user). In other words air in flow to a user's respiratory system is achieved by positive pressure "push" at all points in the machine mediated inspiratory respiratory cycle. Recall that conventional CPAP, although using positive pressure may require alveolar pressure below the prescribed mask pressure during positive pressure recoil during inspiration. Practically, this may provide a prescribed pressure advantage of the current design over standard CPAP or bi-level pressure therapy. This apart the device is aimed to deliver physiologic sensible breathing and hence a more natural user experience concomitant with therapeutic pressure delivery. It can be appreciated that the minimum pressure will be governed also, in addition to expiratory air flow characteristics as mentioned previously, by the required upper pressure and the difference between this value and the optimum swing or pressure difference to provide total ventilatory support. Hence the lower value may need to be increased to avoid over ventilation.

FIG. 2 shows possible lung volume and device pressure profile during normal operation when pressures are applied over a range of lower and upper pressures.

An important feature of the device is that inspiratory drive by the patient is rendered substantially redundant and there is no inspiratory triggered event as this is effectively muted by lung inflation and ventilatory support. This is undertaken entirely by the device. Furthermore, since the device aims to pace or pre-empt the user's respiratory centre the need to monitor the user's upper airway directly or in isolation becomes redundant as the device uses as much pressure as required to move the required volumes into and out of the lungs.

In use a period of habituation and respiratory training on this therapy may be required. It also possible that typical settings, such as usual minute ventilation values, once derived may be initiated immediately on donning the mask or may be increased progressively to enable the user time to become accustomed to the pressure profile. The user is able at any time to breath at their own rate or depth during wakefulness so synchronisation is always maintained with the device. During sleep, background respiratory support will be entirely or substantially managed by the device.

During typical use in treatment of sleep apnea, a possible means to commence a treatment session may include an initial period where upper pressure will be slowly increased from a base pressure, between 0 and 4 cm H2O (selectable). On a user initiated exhalation impulse the pressure will be allowed to proceed, as discussed, to the initial base level and then returned back to the upper pressure after a desired exhaled volume has been achieved. The upper pressure will continue to be increased, possibly over a period of several minutes or longer until inspiratory airflow due to effort at the upper level is inhibited or can be comfortably eliminated during wakefulness; there is no preset upper limit, although this may be set optionally. It is expected to be typically around 10 cm H20 and will vary between users. This level of support will also be in keeping with the moving average minute ventilation measured during a period of previous period of quiet breathing. The pressure profile will then look as in FIG. 2.

When used for treatment of chronic obstructive pulmonary disease (COPD) including acute exacerbations, the device would likely be initiated in a different way depending on patient symptoms and degree of breathlessness and if the device is designed to eliminate sleep hypoventilation. The device would however commonly operate in obstructive diseases to automatically set the lower pressure above iPEEP and maintain an upper pressure level sufficient to eliminate inspiratory effort and provide maximal respiratory muscle unloading as well as provide respiratory support based on target ventilatory parameters. Starting regimes could be selected by the caregiver or user to provide rapid adoption of target values as required by the user. It should be noted however that establishing a target lower pressure to overcome iPEEP is not an essential feature of the invention.

Clinically, sleep apnea in conjunction with sleep hypoventilation is commonly seen in obesity, lung disease or heart failure. Sleep apnea and hyperventilation may also be seen in heart failure. In these cases, prior to sleep, some background support can be provided initially where the amount of initial support will be user dependent and provided according to individual comfort. A moving average of ventilation may be obtained during this period. On falling asleep if ventilation is subsequently calculated to be too high compared to a past moving average of ventilation, the difference between an upper and lower level must be decreased. Remembering also that it is desirable to maintain the airway open, while the upper pressure is designed to inhibit inspiratory effort and if that level, the lower pressure will then need to be increased if it is already at a minimum level. Increasing the lower pressure, although in excess of that required to maintain the airway open, will reduce the amount of ventilatory support while the upper pressure is maintained to limit spontaneous effort. Similarly, if the minute ventilation is found to be too low, then the upper pressure will needed to be increased or the lower pressure reduced subject to its minimum as discussed.

Figure 3:
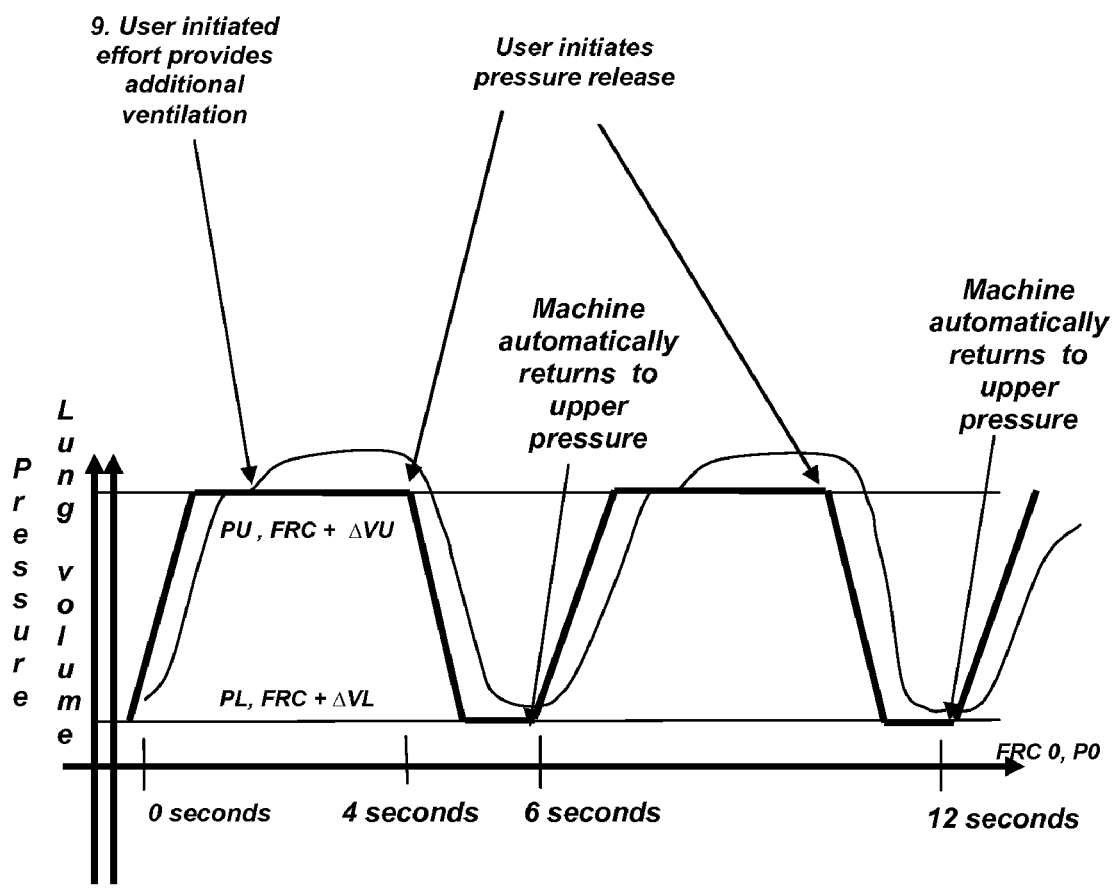
FIG. 3: Pressure and lung volume profile with time where pressure is increased below total ventilatory requirements and user provides additional effort to augment total ventilations in line with requirements.

In yet a further embodiment of the method, a pressure profile is applied to user's airway shown in FIG. 3. Heavy line represents administered pressure, lighter line represents lung volume. Times are illustrative only and may be shorter or longer than shown. Rather than aiming to totally inhibit inspiratory effort and provide all support it is the aim of the device to provide a substantial or targeted level of support based on quiet breathing (a moving average estimate). In this way additional inspiratory effort may be under the control of the user as shown at 9. The device then provides a minimum background level of support and additional efforts at an upper pressure level are monitored to ensure absence of snore and other indicators of inspiratory flow resistance such as flow limitation. To ensure adequate ventilation and airway patency, the upper pressure and lower pressure may be adjusted. For example if airway stability is achieved through an appropriate upper pressure but ventilation is excessive then the lower pressure may be increased, either independently or in conjunction with an upper pressure, which may act to dampen user initiated hyperventilatory efforts through lung expansion and reduced machine support. If ventilation is inadequate then the lower pressure may be reduced, and if this lower pressure is at a minimum level the upper pressure may be increased.

Figure 4:
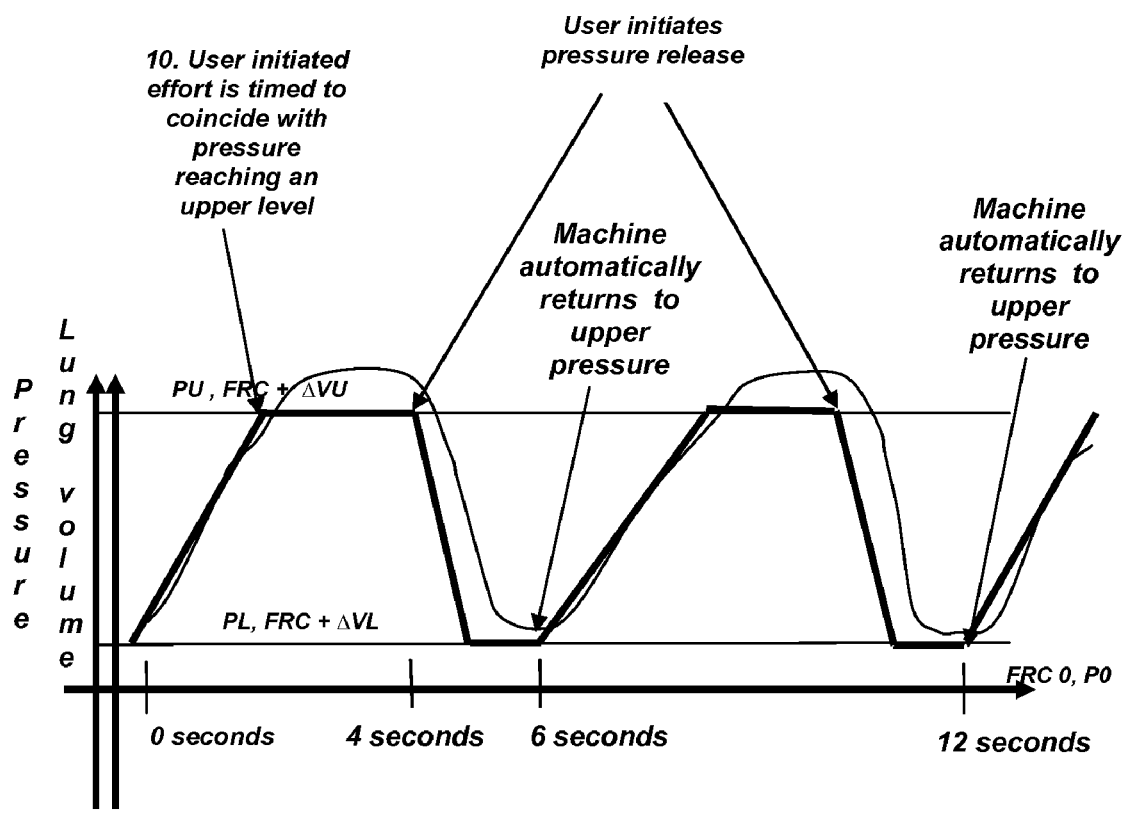
FIG. 4: Pressure and lung volume profile with time where pressure is increased such that the rate of increase in pressure is matched to coincide with commencement of a user's inherent effort.

In yet a further embodiment of the method, a pressure profile is applied to user's airway shown in FIG. 4. Heavy line represents administered pressure, lighter line represents lung volume. Times are illustrative only and may be shorter or longer than shown. A partial level of support is provided wherein a target upper pressure is reached at a time point coincident with commencement of a user's inspiratory effort, that is when a user will take over the device's inspiratory support. This will be based on adjusting the rate of pressure increase based on past cycling rates, the level of a lower and upper pressure as well as the smoothness of the delivered volume time curve at 10 (this may also be achieved by monitoring flow). In the absence of user effort, rate of volume increase will be proportional to the rate of pressure increase provided by the device (Ps) with time (t) that is $dPs/dt$, where proportionality is dependent upon the mechanical properties of a user's respiratory system, hysteresis and surface tension effects. Of interest are only incremental user sponsored breathing efforts that will increase flow above that provided by the device while $dPs/dt$ is greater than or equal to zero. Gas volume, entering into a user's respiratory system $V(t)$, volume as a function of time (t) or flow is then monitored to ensure that the rate of increase in pressure provides a rate of change of volume with time or flow versus time that is as smooth and seamless as possible for all periods while $dV/dt>0$, that is while lung volume is increasing. It is evident that it may not always be possible to match exactly the rate of volume change provided by the device and a user's effort when $dPs/dt$ is equal to a constant for $Ps>0$, rather the aim is to ensure that the transition between completion of machine supported volume change coincides as closely as possible with commencement of user inspiratory effort. Notwithstanding that algorithms may be incorporated to provide non linear rates of pressure change to match the rate of volume change from machine pressure support to user initiated effort. Furthermore, snore and other indicators of inspiratory flow resistance such as flow limitation are monitored as before as well as ventilatory considerations as described above to ensure a targeted level of an upper and lower pressure.

It is evident that the computerised blower apparatus to be operated according to the conditions of the methods as described will consist of pressure and flow sensors as well as analogue and digital signal conditioning hardware and software and may be constructed by techniques typically described in, but not limited to, the prior art.

In summary the invention in its preferred embodiment aims to:

a) minimise patient respiratory effort so the invention provides most or all motive power for air movement into and out of the lungs by adapting operation to limit movement into the lungs by either pressure recoil or inspiratory effort. While the shape of part or all of any inspiratory effort flow time curve may be included it is envisaged this would in fact be a redundant feature as the device aims to provide optimal ventilation by providing positive pressure from the pressure source. However this may be provided as a further embodiment as discussed later.

b) ideally determine a minimum pressure which is just sufficient to maintain airway patency during expiratory outflow and hence for allowing elastic recoil movement of air from the lungs. In this way continuous communication throughout the airway system is achieved. This may be maintained by continuous measurement and assessment of the shape of airflow versus time curve exiting the user's airway after compensating for vent and mask leak. This lower pressure will then represent the pressure below which no further elastic air flow from the user's respiratory system can occur. In an open airway at atmospheric pressure this pressure will be equal to zero. It should be noted however that this is not an essential feature of the device but rather a potentially desirable one.

c) determine pressure limits in addition to those as defined in a) and b) above which provides adequate minute ventilation based on quiet awake or somnolent breathing and other anatomical features, such as height, weight, tidal volume as required.

d) finding pressure limits and or rate which servo controls respiration, by being just above, below or at the patient's own respiratory rate or inherit ventilatory needs.

e) provide pressure time profile which is optimally servo controlled by flow to provide a normal pattern of lung filling and emptying. This may range from a half square wave to a ramp or some other profile.

f) automatically restore administered pressure to an upper pressure from a lower pressure after lung emptying has been achieved.

g) While the invention has been described with reference to a range of embodiments as described above, it will occur to those skilled in the art that various modifications and additions further to the disclosed methods discussed herein may be made without departing from the spirit and scope of the invention.

I claim:

1. A method of ventilating a user comprising: providing an atmospherically vented mask or nasal prongs; cycling administered pressure between and including an upper pressure and a lower pressure to a user's airway through the vented mask or nasal prongs, the lower pressure being greater than atmospheric pressure by: maintaining the lower pressure only for sufficient time to allow a prior administered gas volume to be at least substantially expelled from a user's respiratory system by its elastic recoil; commencing a transition from the lower pressure to the upper pressure immediately upon the prior administered gas volume having been at least substantially expelled from a user's respiratory system by its elastic recoil, and sensing either flow or pressure to detect a need to initiate lung emptying and initiating a transition from the upper pressure to the lower pressure, or initiating the transition in response to a minimum background expiratory rate.

2. The method as claimed in claim 1, wherein a rate at which the prior administered gas volume is at least substantially expelled from the user's respiratory system by its elastic recoil is servo-regulated by a computer-controlled pressure source.

3. The method as claimed in claim 1, wherein cycling is carried out with the administered pressure from the lower pressure to the upper pressure being servo-regulated by a computer-controlled pressure source.

4. The method as claimed in claim 1, further comprising setting a minimum lower pressure level to maintain the user's airway substantially unrestricted or unobstructed.

5. The method as claimed in claim 1, further comprising selectively increasing or decreasing a level of supported ventilation to ensure that, over a single respiratory cycle, a total ventilation is equal to the level of supported ventilation and a user's own effort is targeted to provide a time average equivalence with a moving average of the user's past minute ventilation.

6. The method as claimed in claim 1, further comprising progressively decreasing the upper and lower pressures after a period of airway stability.

7. The method as claimed in claim 1, further comprising setting a minimum upper pressure at a level of support selected to at least minimize patient inspiratory effort.

8. The method as claimed in claim 1, further comprising setting a minimum upper pressure at a level of support that is less than a moving average of the user's past minute ventilation and that requires additional inspiratory effort by the user to fulfill ventilatory requirements.

9. The method as claimed in claim 8, further comprising adjusting the minimum upper pressure to eliminate inspiratory flow abnormalities.

10. The method as claimed in claim 8, further comprising setting a rate of pressure rise to the upper pressure from the lower pressure to ensure that the upper pressure is reached prior to or concomitantly with the user beginning the additional inspiratory effort.

11. The method as claimed in claim 1, wherein the atmospherically vented mask or nasal prongs are configured to actively and substantially direct expired air to the atmosphere.

* * * * *